US012703853B2

(12) United States Patent
Kaps et al.

(10) Patent No.: US 12,703,853 B2
(45) Date of Patent: Aug. 11, 2026

(54) METHOD FOR CULTIVATION OF CARTILAGE AND SPHEROIDS THEREOF

(71) Applicant: CO.DON GmbH, Leipzig (DE)

(72) Inventors: Christian Kaps, Berlin (DE); Giulietta Roël, Berlin (DE); Claudia Eschen, Berlin (DE)

(73) Assignee: CO.DON GmbH, Leipzig (DE)

(*) Notice: Subject to any disclaimer, the term of this patent is extended or adjusted under 35 U.S.C. 154(b) by 909 days.

(21) Appl. No.: 17/615,278

(22) PCT Filed: Jun. 2, 2020

(86) PCT No.: PCT/EP2020/065137
§ 371 (c)(1),
(2) Date: Nov. 30, 2021

(87) PCT Pub. No.: WO2020/240040
PCT Pub. Date: Dec. 3, 2020

(65) Prior Publication Data

US 2022/0220443 A1 Jul. 14, 2022

(30) Foreign Application Priority Data

May 31, 2019 (EP) .................................... 19177770

(51) Int. Cl.
*C12N 5/077* (2010.01)
*A61L 27/36* (2006.01)

(52) U.S. Cl.
CPC ........ *C12N 5/0655* (2013.01); *A61L 27/3612* (2013.01); *A61L 27/3654* (2013.01);
(Continued)

(58) Field of Classification Search
CPC .............. C12N 5/0655; C12N 2513/00; A61L 27/3612; A61L 27/3654; A61L 2430/06;
(Continued)

(56) References Cited

U.S. PATENT DOCUMENTS 7,887,843 B2 2/2011 Libera et al.
2003/0153078 A1* 8/2003 Libera .................... A61P 19/00 435/395

(Continued)

FOREIGN PATENT DOCUMENTS

CN 1661010 A 8/2005
CN 101056974 A 10/2007

(Continued)

OTHER PUBLICATIONS

Anderer et al., "In Vitro Engineering of Human Autogenous Cartilage", Journal of Bone and Mineral Research, Blackwell Science, vol. 17, No. 8, Aug. 1, 2002, pp. 1420-1429.

(Continued)

*Primary Examiner* — Tracy Vivlemore
*Assistant Examiner* — Lauren K Van Buren
(74) *Attorney, Agent, or Firm* — Morse, Barnes-Brown & Pendleton, P.C.; Stanley F. Chalvire, Esq.; Russell L. Widom

(57) ABSTRACT

The present invention relates to a method for propagating or enriching cartilage cells and providing spheroids thereof, wherein the spheroids are useful for an autologous chondrocyte implantation (ACI) product. Hence, the invention in particular relates to the production of spheroids from articular cartilage and use thereof.

11 Claims, 4 Drawing Sheets

(52) U.S. Cl.
CPC ....... *A61L 2430/06* (2013.01); *A61L 2430/24* (2013.01); *C12N 2513/00* (2013.01)

(58) Field of Classification Search
CPC . A61L 2430/24; A61L 27/3608; A61K 35/32; A61P 19/08; A61P 19/00
See application file for complete search history.

(56) References Cited

U.S. PATENT DOCUMENTS

| | | | | |
|---|---|---|---|---|
| 2009/0176304 | A1 | 7/2009 | Smith et al. | |
| 2010/0028308 | A1* | 2/2010 | Knipper | A61P 19/02 435/395 |
| 2011/0020798 | A1 | 1/2011 | Holtzman et al. | |
| 2014/0178994 | A1 | 6/2014 | West et al. | |
| 2014/0234964 | A1 | 8/2014 | West et al. | |
| 2015/0344847 | A1 | 12/2015 | Malinin | |
| 2020/0147269 | A1 | 5/2020 | Roël et al. | |

FOREIGN PATENT DOCUMENTS

| | | | |
|---|---|---|---|
| CN | 101317089 | A | 12/2008 |
| CN | 101616693 | A | 12/2009 |
| CN | 101657536 | A | 2/2010 |
| CN | 101680881 | A | 3/2010 |
| CN | 103223194 | A | 7/2013 |
| CN | 103881969 | A | 6/2014 |
| CN | 103987855 | A | 8/2014 |
| CN | 105209607 | A | 12/2015 |
| CN | 106834223 | A | 6/2017 |
| CN | 109152864 | A | 1/2019 |
| CN | 111032859 | A | 4/2020 |
| DE | 10013223 | A1 | 10/2001 |
| DE | 102009025347 | A1 | 12/2010 |
| EP | 2390346 | A1 | 11/2011 |
| EP | 2345450 | B1 | 9/2016 |
| WO | 2004028339 | A2 | 4/2004 |
| WO | 2005095585 | A1 | 10/2005 |
| WO | 2011025367 | A1 | 3/2011 |
| WO | 2013010045 | A1 | 1/2013 |
| WO | 2016099453 | A1 | 6/2016 |
| WO | 2019/002148 | A1 | 1/2019 |
| WO | 2020240040 | A1 | 12/2020 |

OTHER PUBLICATIONS

Dehne et al., "Chondrogenic differentiation potential of osteoarthritic chondrocytes and their possible use in matrix-associated autologous chondrocyte transplantation", Arthritis Research and Therapy, Biomed Central, vol. 11, No. 5, Sep. 2, 2009, p. R133.

Huang et al., "Cell-based tissue engineering strategies used in the clinical repair of articular cartilage", Biomaterials, vol. 98, Apr. 26, 2016, pp. 1-22.

International Preliminary Report on Patentability received for PCT Patent Application No. PCT/EP2020/065137, mailed on Sep. 23, 2021, 12 pages.

International Search Report and Written Opinion received for PCT Patent Application No. PCT/EP2020/065137, mailed on Oct. 8, 2020, 13 pages.

Kuroda et al., "Studies on cartilage cells in vitro—II. Changes in aggregation and in cartilage-forming activity of cells maintained in monolayer cultures", Experimental Cell Research, vol. 35, No. 2, Jul. 1, 1964, pp. 337-348.

Niemeyer et al., "A Prospective, Randomized, Open-Label, Multicenter, Phase III Noninferiority Trial to Compare the Clinical Efficacy of Matrix-Associated Autologous Chondrocyte Implantation With Spheroid Technology Versus Arthroscopic Microfracture for Cartilage Defects of the Knee", Orthopaedic Journal of Sports Medicine, vol. 7, No. 7, Jul. 1, 2019, pp. 1-11.

Schubert et al., "Long-term effects of chondrospheres on cartilage lesions in an autologous chondrocyte implantation model as investigated in the SCIO mouse model", International Journal of Molecular Medicine, vol. 23, No. 4, Mar. 16, 2009, pp. 455-460.

Becher et al., "Safety of three different product doses in autologous chondrocyte implantation: results of a prospective, randomised controlled trial", Journal of Orthopedic Surgery and Research, 12: 71, (2017).

Chi Guang-fan et al., "Experimental study of repair of articular cartilage full-thickness defect by tissue engineered autograft", Chin J End, 23(6): 516-519 (2004).

Chua et al., "Insulin-Transferrin-Selenium Prevent Human Chondrocyte Dedifferntiation and Promote the Formation of High Quality Tissue Engineering Human Hyaline Cartilage", European Cells and Materials, 9: 58-67, (2005).

Kawaki et al., "Cooperative Regulation of Chondrocyte Differentiation by CCN2 and CCN3 Shown by a Comprehensive Analysis of the CCN Family Proteins in Cartilage", Journal of Bone and Mineral Research, 2311: 1751-1764 (2008).

Martin et al., "In vitro development of personalized cartilage microtissues uncovers an individualized differentiation capacity of human chondrocytes", Experimental Biology and Medicine, 242: 1746-1756, (2017).

Suzuki et al., "The metabolism of hyaluronan in cultured rabbit growth plate chondrocytes during differentiation", Biochimica et Biophysica Acta, 1743: 57-63, (2005).

Yang et al., "Application of mesenchymal stem cell-derived microvesicles in the repair of articular cartilage damage", Journal of Practical Orthopaedics, 21(1): 59-61, (2015).

Zipper et al., "Development of chick limb bud chondrocutes in cell culture: Morphologic and oxidative metabolic observations", Clin Orthop Relat Res., 155: 186-195, (1981).

Examiner's Report issued in Canadian application No. 3,067,770 dated Aug. 22, 2025.

Examiner's Report issued in Canadian application No. 3,141,639 dated Aug. 1, 2025.

Office action and search report issued in Eurasian application No. 202591404 dated Sep. 8, 2025.

Office Action issued by Korean Patent Office for Korean patent application No. 1020217043019 Sep. 30, 2025.

Notice of Allowance and Issue Fee Due for U.S. Appl. No. 16/625,937 dated Jan. 6, 2026.

Bartz et al., "An ex vivo human cartilage repair model to evaluate the potency of a cartilage cell transplant", Journal of Translational Medicine, 14(1):1-15, (2016).

Bennett et al., "HPV Status-independent association of alcohol and tobacco exposure or prior radiaiton therapy with promoter methylation of FUSSEL18, EBF3, IRX1, and SEPT9, but not SLC5A8, in head and neck squamous cell carcinomas", Genes Chromosomes & Cancer, 49:319-326, (2010).

Bin et al., "Cell surface markers during chondrogenic indution of mesenchymal stem cells derived from mouse hair follicle in vitro," Chinese Journal of Tissue Engineering Research, 16(32):5973-5977, (Aug. 5, 2012).

El-Magd, et al., "Bmp4 regulates chick Ebf2 and Ebf3 gene expression in somite development," Development, Growth & Differentiation, 55:710-722, (2013).

Feng et al., Differential expression gene of rat bone marrow mesenchumal stem cells and chondrocytes screened by gene chip technique, Journal of Clinical Rehabilitative Tissue Engineering Research, vol. 12, No. 10, Mar. 5, 2009.

Ito, "Evaluation of reference genes for human chondrocytes cultured in several different thermal environments", Int J. Hyperthermia, 30(3): 210-216, (2014).

Iwai et al., "Ex vivo cartilage defect model for the evaluation of cartilage regeneration using mesenchymal stem cells", Journal of Bioscience and Engineering, 11:357-364, (2010).

Kieslinger et al., "EBF2 Regulates Osteoblast-Dependent Differentiation of Osteoclasts", Developmental Cell, 9:757-767, (2005).

Martin et al., "In vitro development of personalized cartilage microtissues uncovers an individualized differentiation capacity of human chondrocytes," Experiental Biology Medicine, 242(18) :1746-1756, (2017).

(56) References Cited

OTHER PUBLICATIONS

Martinez et al., "Redifferentiation of in Vitro Expanded Adult Articular Chhondrocutes by Combining the Hanging-Drop Cultivation Method with Hypoxic Environment", Cell Transplantation, 17(8):987-996, (2008).
Murphy et al., "Engineering a fibrocartilage spectrum through modulation of aggregate redifferentiation," Cell Translant, 24(2): 235-245, (2015).
Ng, et al., "Extracellular matrix components and culture regimen selectively regulate cartilage formation by self-assembling human mesenchymal stem cells in vitro and in vivo," Stem Cell Research & Therapy, 7(183):1-12, (2016).
Pfaffl, "A new mathematical model for relative quantification in real-time RT-PCR," Nucleic Acids Research, 29(9):2002-2007, (2001).
Roos et al., "The Knee injury and Osteoarthritis Outcome Score (KOOS): from joint injury to osteoarthritis," Health and Quality of Life Outcomes, 1:1-8, (Nov. 3, 2003).
Vapniarsky et al., "Tissue engineering toward temporomandibular joint disc regeneration," Sci Transl Med., 10(446):1-28, (2018).
Wang et al., "Advance in autologous chondrocyte implantation for repair of articular cartilage injury," Orthopedic Journal of China, 23(4):328-331, (2015).
Wikipedia Reference Genes (2024).
Zhou et al., "Bone morphogenetic protein-7 promotes chondrogenesis in human amniotic epithelial cells", International Orthopaedics, 35(6):941-948, (2010).
Notice of Allowance and Issue Fee Due for U.S. Appl. No. 16/625,937, dated Mar. 13, 2025.
Martin et al., In vitro development of personalized cartilage microtissues uncovers an individualized differentiation capacity of human chondrocytes, Exp Biol Med (Maywood). Dec. 2017; 242(18):1746-1756.†
Vapniarsky et al., Tissue engineering toward temporomandibular joint disc regeneration, Sci Transl Med. Jun. 20, 2018;10(446):eaaq1802, pp. 1-28.†
Murphy et al., Engineering a fibrocartilage spectrum through modulation of aggregate redifferentiation. Cell Transplant. 2015;24(2): pp. 235-245 (Online prepub date: Dec. 30, 2013).†

* cited by examiner
† cited by third party

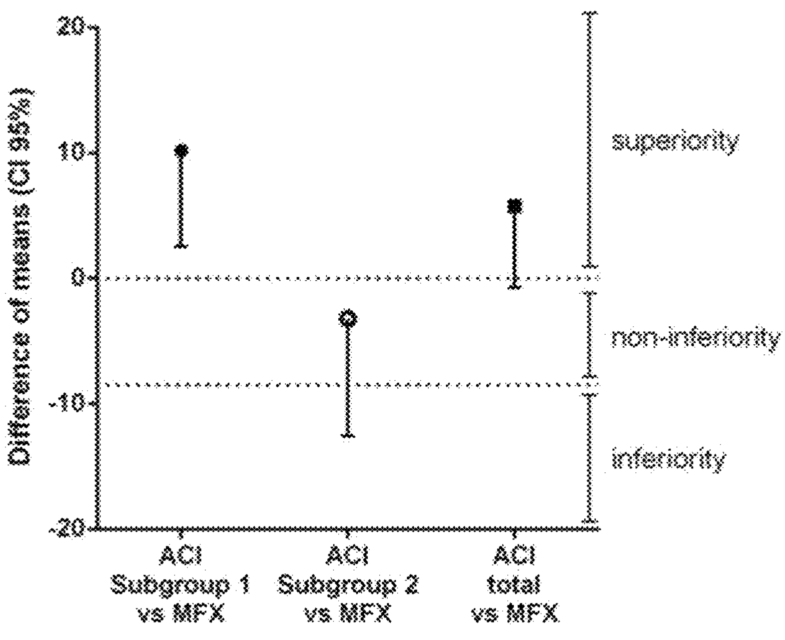
Fig. 4
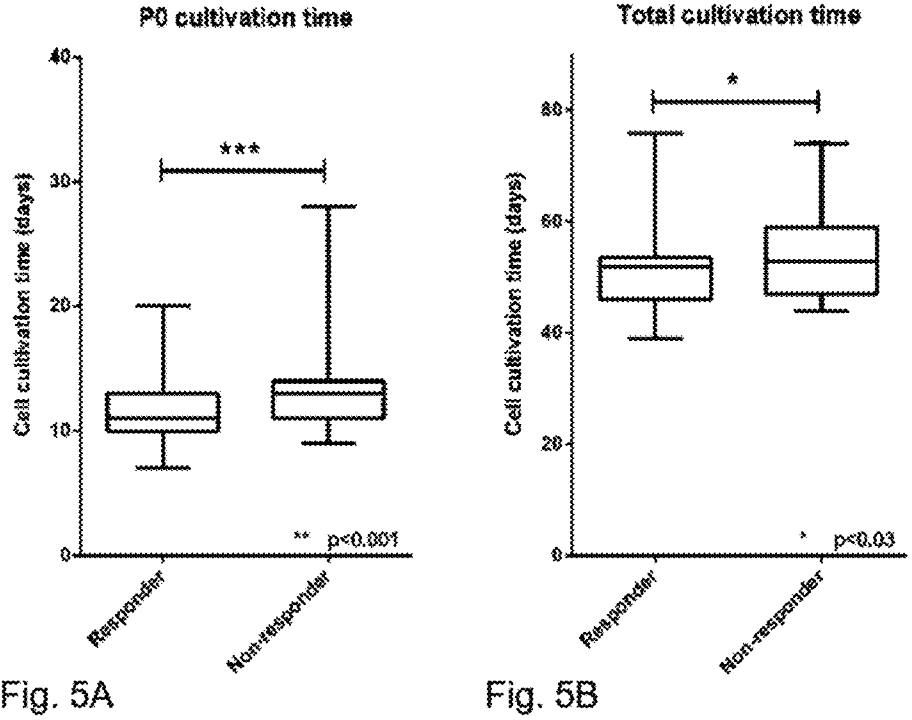
Fig. 5A
Fig. 5B

METHOD FOR CULTIVATION OF CARTILAGE AND SPHEROIDS THEREOF

CROSS-REFERENCE TO RELATED APPLICATIONS

This application is a national stage application (under 35 U.S.C. § 371) of PCT/EP2020/065137, filed Jun. 2, 2020, which claims benefit of European Application No. 19177770.5, filed May 31, 2019, both of which are incorporated herein by reference in their entirety.

The present invention relates to a method for propagating or enriching cartilage cells and providing spheroids thereof, wherein the spheroids are useful for an autologous chondrocyte implantation (ACI) product. Hence, the invention in particular relates to the production of spheroids from articular cartilage and use thereof.

Although articular cartilage demonstrates notable resilience, this tissue is unable or is hardly able to repair itself, and untreated legions may lead to osteoarthritis. This low potential for spontaneous regeneration has led to the development of cell therapies, such as autologous chondrocyte implantation (ACI), with the aim of providing a functional and pain-free repair of articular cartilage defects. Techniques of this type, however, cannot guarantee cartilage regeneration, and there have not previously been any adequate long-term studies. Consequently, there is a high need for methods for cartilage regeneration, for example in young active patients with traumatic legions or even with systems of cartilage degeneration.

Numerous studies have been carried out with chondrocytes which have been isolated from cartilage of cattle, rabbits or sheep. The obtained data and animal-based concepts of this type, however, cannot be transferred to the human situation. Detailed biochemical and molecular studies with human chondrocytes have been hindered by a series of factors, such as the lack of availability of human tissue in conjunction with the very small number of cells available in a biopsy, the limited proliferation capacity and the high phenotypic instability of cultivated chondrocytes.

A chondrocyte (synonymous: cartilage cell) is a cell that originates from chondroblasts and that is established in the cartilage tissue. Together with the intercellular substances (extra cellular matrix (ECM)), the chondrocytes form the primary components of cartilage.

Native articular cartilage tissue has a composition of the extracellular matrix formed of approximately 60 to 80% water in relation to the wet weight of the articular tissue. The high water content is important for the mechanical load-bearing ability of the cartilage tissue and, together with the proteoglycans, is important for the “sponge effect”. Besides water, natural articular cartilage contains the structural macromolecules of the matrix, such as collagens, proteoglycans and non-collagen proteins. Here, the structural macromolecules account for approximately 20 to 40% of the wet weight of the articular cartilage tissue.

It is already known, for example by mimicry of certain processes of embryonal development, for example to cultivate human cartilage cells three-dimensionally on an agarose substrate, such that cell aggregates are produced which are superior to the monolayer cells in terms of their differentiation ability and which for example have cartilage-like properties. These properties, which reflect the native articular cartilage tissue as accurately as possible, are characterised by the expression of collagen II (primary structural protein in the extracellular matrix of hyaline cartilage), of proteoglycans, for example aggrecan, and the intracellular chondrocyte-specific protein S100. In addition, it is desirable for the expression of collagen I, which is necessarily up-regulated during the cell multiplication phase in the monolayer culture, to be reduced again in the cell aggregates, since this protein is practically absent in native articular cartilage. The cell aggregates thus generated (spheroids) have been offered since 2002 for example by the applicant (co.don AG) in order to therefore treat primarily smaller cartilage defects caused by injury. To this end, natural articular cartilage tissue is removed from the patient and the cells isolated therefrom are transplanted as spheroids following multiplication and 3D culture. An autologous chondrocyte implantation (ACI) product is known as Spherox®.

The cultivation of human cells in the form of three-dimensional cell aggregates, in particular in the form of what are known spheroids, is already authorised for clinical use in humans, for example as autologous cartilage transplant (DE 100 13 223). DE 100 13 223 concerns a method for the in vitro production of three-dimensional cartilage tissue and bone tissue from bone stem cells, cartilage stem cells or mesenchymal stem cells. Here, the cells are firstly cultivated in a monolayer culture and are then cultivated in suspension until a cell aggregate is produced that contains at least 40 vol % extracellular matrix, in which differentiated cells are embedded. In the method, cell aggregates are produced by cultivating cells for at least 1-2 weeks in cell culture vessels coated with agarose.

U.S. Pat. No. 7,887,843 B2 discloses a method for the in vitro production of three-dimensional cartilage tissue and bone tissue, wherein spheroids are produced from bone stem cells, cartilage stem cells or mesenchymal stem cells by cultivating $1\times10^5$ cells for at least two weeks. The spheroids produced in accordance with U.S. Pat. No. 7,887,843 B2 have a diameter of 500-700 μm after one week. In accordance with this method, $1\times10^5$ or $2\times10^5$ chondrocytes are cultivated for 5 days, 2 weeks 1, 2 and 3 months in order to produce spheroids.

According to the invention, patient-derived tissue biopsies are used as starting material. The tissue-building cells are isolated from the biopsies according to conventional methods, using enzymatic digestion of the tissue, migration, or reagents recognizing the target cells.

According to the invention, these cells are then subjected to stationary culturing, wherein the cells are firstly cultivated in a substrate supported monolayer culture (2-dimensional) and are then cultivated in suspension in a simple fashion free of a substrate, using conventional culture medium in cell culture vessels in particular with hydrophobic surface, until a three-dimensional cell aggregate is formed which includes at least 40% by volume and up to a maximum of 95% by volume of extracellular matrix (ECM) having differentiated cells embedded therein. Such formed aggregates are called spheroids in the meaning of the present invention.

As cell culture vessels in accordance with the invention, the cultivation step in suspension requires the use of those having a hydrophobic, i.e., adhesion-preventing surface, such as polystyrene or Teflon or the like. Cell culture vessels with a non-hydrophobic surface can be preferably hydrophobized by coating with agar or agarose. Further additives are not required. Preferably, 96-well plates are used as cell culture vessels.

It is remarkable that the cells integrated in the spheroids produced according to the invention survive, and that the cells inside do not necrotize even after an advanced period of culturing. With increasing time of cultivation, the cells inside the aggregates undergo differentiation to form spheroids consisting of ECM, differentiated cells and a peripheral proliferation zone. The process of formation of the tissue-specific matrix with embedded cells is highly similar to the process of tissue formation or neogenesis and reorganization in the body. During differentiation in cell culture, the spacing of the aggregated cells increases due to formation of the tissue-specific matrix. A tissue histology develops inside the spheroids which is highly similar to natural tissue. As in natural cartilage, the cells inside the spheroids are supplied with nutrients by way of diffusion only. During the further course of spheroid production, a zone of cells capable of proliferation and migration is formed at the boundary of the spheroids. This zone is invaluably advantageous in that following incorporation of the spheroids in defects, the cells situated in this peripheral zone are capable of migrating to make active contact with the surrounding tissue and/or enable integration of the tissue produced in vitro in the environment thereof. Thus, the tissue-specific cell aggregates produced are excellently suitable for use in the treatment of tissue defects and in the in vitro and in vivo neogenesis of tissue.

However, it is an object of the invention to improve the known method and obtainable spheroids hereto, in particular to reduce the outcome of patients or patient populations of non-responders or therapeutic failures and to provide a method for higher patient's clinical safety. Such a non-responder patient can be identified by a so-called change of KOOS value of 8-10 points compared to the pre-operative situation (Roos E M, Lohmander L S. The Knee injury and Osteoarthritis Outcome Score (KOOS): from joint injury to osteoarthritis. Health Qual Life Outcomes 2003; 1: 64.).

Surprisingly, the inventors have concluded from a study including 120 patients (NCT01225575 and NCT0122259) that method related operational ranges or process parameters have a valuable impact on the spheroid's efficacy.

Hence, the underlying technical problem is solved by at least one claim, wherein the cultivation time is a critical feature.

Particularly, the invention relates to a method for propagating or enriching cartilage cells and providing spheroids thereof comprising the steps:

a.) isolating cartilage cells from tissue of human or animal origin,
b.) cultivating cells from a.) in expanding a monolayer (2D), wherein the monolayer is placed on a substrate,
c.) taking the monolayer from a.) and cultivating said cells in a suspension in a 3D environment,
d.) wherein the total cultivation time of step b.) and step c.) is equal or less than 55 days calculated from the starting time of step a.), and wherein the time duration of step b.) is more than 10 days.
e.) selecting the obtained spheroids.

In a preferred embodiment of the invention, the time duration of step b.) is less than 38 days and/or the time duration of step c.) is less than 28 days.

In a preferred embodiment of the invention, the time duration of step b.) is more than 10 days or more than 16 days or more than 20 days and less than 38 days.

In a preferred embodiment of the invention, the time duration of step b.) is more than 10 days and equal or less than 16 days.

Surprisingly, the spheroids obtained are optimized respectively amount and size (diameter) and hence spheroids of best efficacy are provided leading to a sustainable reduction of patients or patient populations of non-responders or therapeutic failures, in particular patients with a KOOS value <8 as outlined below.

Hence, the spheroids obtained and selected consist of cells in the optimized range of 3,000 to 200,000 cells, preferably in the range of 3,500 to 75,000 cells.

Moreover, spheroid's diameter (size) is in the optimized range of 100 to 1,000 μm, preferably 200 to 900 μm or preferably 240 to 870 μm.

Such spheroids obtained or selected are most effective and curable for the treatment of 10 $cm^2$ defects, wherein an amount of 10-70 spheroids/$cm^2$ are used.

The spheroids obtained in this way are processed further to form pharmaceutical preparations.

BRIEF DESCRIPTION OF THE DRAWINGS

FIG. 4 illustrates the superiority/non-inferiority analysis of Subgroups 1 and 2 of the study;

FIG. 5A illustrates the P0 cultivation times for responders and non-responders; and FIG. 5B illustrates the total cultivation times for responders and non-responders.

Within the meaning of this invention, "substrate" shall mean any material suitable for carrying a monolayer.

Cultivation is performed using cell culture conditions and culture media that are known to one of ordinary skill in the art (Schubert T, Anders S, Neumann E, Schölmerich J, Hofstädter F, Grifka J, Müller-Ladner U, Libera J, Schedel J. Int J Mol Med. 2009 April; 23(4):455-60.).

The method of the invention permits the advantageous enrichment and propagation of cartilage cells and spheroids thereof.

Figure 1A:
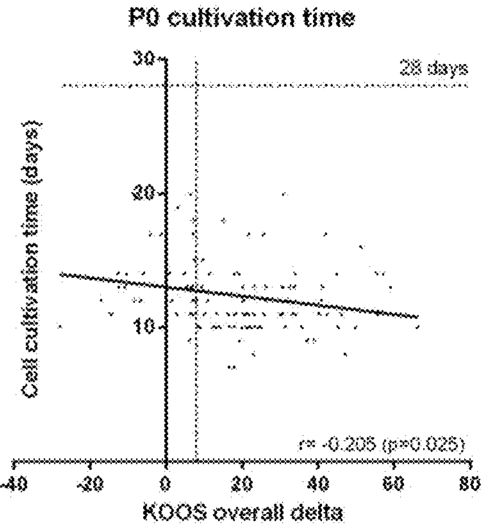
FIG. 1A illustrates the correlation of clinical outcome with P0 cell cultivation times.
Figure 1D:
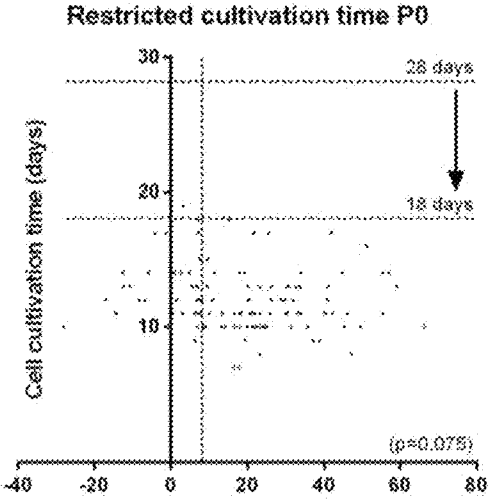
FIG. 1D illustrates the correlation of clinical outcome with restricted P0 cell cultivation times.
Figure 1B:
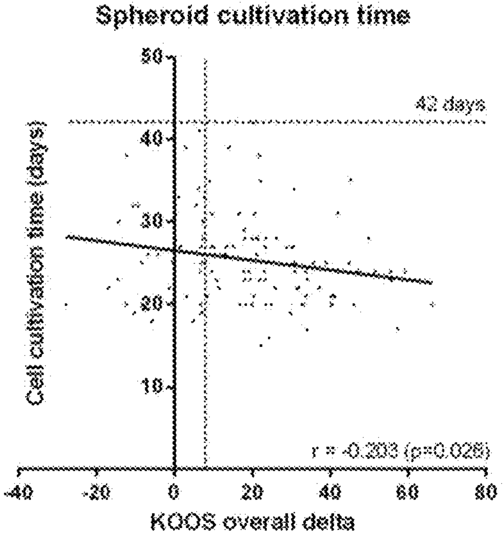
FIG. 1B illustrates the correlation of clinical outcome with spheroid cultivation times.
Figure 1E:
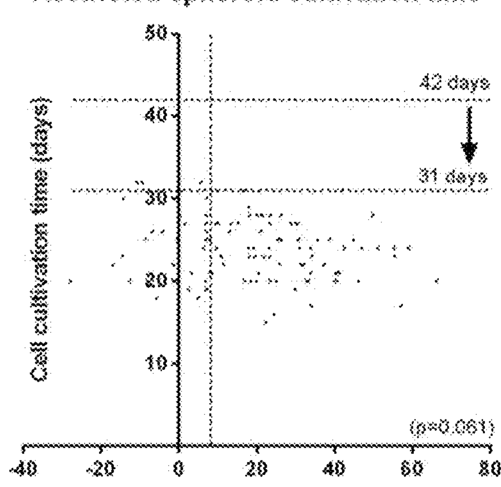
FIG. 1E illustrates the correlation of clinical outcome with restricted spheroid cultivation times.
Figure 1C:
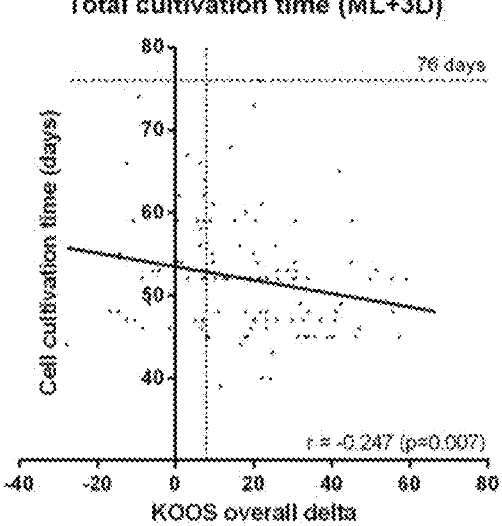
FIG. 1C illustrates the correlation of clinical outcome with total cultivation times.

According to the invention, a negative correlation was found between the KOOS values and process parameters such as the monolayer cultivation time before the first passage (in short: P0) (Spearman, P=0.025) (FIG. 1A), the spheroid cultivation time (in short: 3D) (P=0.026) (FIG. 1C) and the total cultivation time of chondrocytes in monolayer (in short: ML) and spheroids (P=0.007) (FIG. 1E). In FIG. 1 the KOOS overall delta scores are plotted against the cell cultivation times in P0, 3D and ML plus 3D for every spheroid batch of patients, showing the negative correlation (FIG. 1A-C). These initial findings suggest that shorter cultivation times are beneficial for the quality of the product represented by a better clinical outcome after implantation. This is supported by the observation that the non-responder group (KOOS<8) had received spheroid batches that have been manufactured with significant longer cultivation times in P0 compared to the responder group (FIG. 5A). Also, the total cell culture duration of ML and 3D, appeared to be longer on average in the non-responder group (FIG. 5B). This underscores the need to newly define and restrict the operational ranges or process parameters for cell culture time based on study data to avoid a negative impact on the spheroid's efficacy and disadvantage on patient's outcome.

Figure 1F:
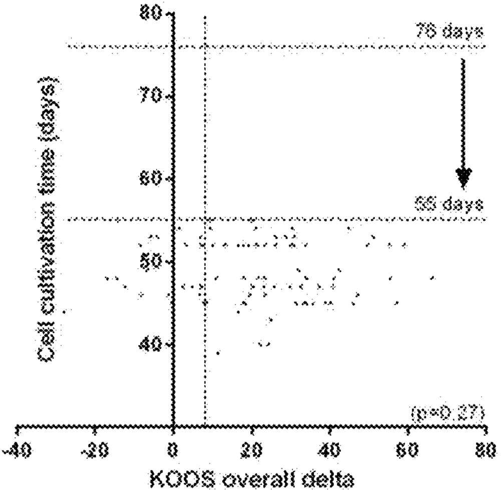
FIG. 1F illustrates the correlation of clinical outcome with restricted total cultivation time.

To determine a provisional maximum time for chondrocyte cultivation, the batches with the longest cultivation time were subsequently deleted from the data set until the negative correlation disappeared (Spearman's correlation coefficient). For the ML cultivation time before the first passage, P0, a maximum cultivation time without a negative effect on clinical outcome was defined at 19 days. However, at 19 days of cultivation in P0 the batch belonged to a non-responder. Therefore, the provisional maximum cultivation time was set at 18 days (FIG. 1D). A provisional maximum allowed time for spheroid cultivation was set at 31 days (FIG. 1E). For the total cultivation time in ML and 3D when those batches that have been cultivated for more than 16 days in P0 and 28 days in 3D were eliminated from the data set only batches with cultivation times until 55 days were left. In this group of patients/batches there was surprisingly found no correlation between total cultivation time and efficacy (FIG. 1F).

Since the correlation coefficients between the clinical outcome and P0, 3D and total cultivation times were very low (−0.2), the batches that were produced with high cultivation times were further analysed for the occurrence of non-responders (KOOS score <8). This revealed a remarkable high non-responder rate of 80% in the group of patients treated with spheroid batches cultivated in ML P0 between 19 and 28 days, and 61.5% for batches cultivated between 16 and 28 days (cf. Table 1). Batches cultivated up until 16 days displayed a non-responder rate of 28%, which is significantly lower compared to the 31.7% of non-responders in the complete clinical study group. Considering the non-responder rate together with the feasibility of cultivation times during manufacturing, the provisional maximum cultivation time was defined at, but not further restricted than 16 days.

The same analysis was performed to define a provisional limit for spheroid cultivation time. After deleting spheroid batches that have been cultivated longer than 32 days from the data set, the negative correlation disappeared (FIG. 1E). However, a provisional limit was set at 31 days since spheroid batches cultivated for 32 days all belonged to non-responders (n=4). Furthermore, patients treated with spheroids cultivated in 3D between 32 and 42 days showed a relatively high non-responder rate of 59% (n=17) (cf. Table 2) underscoring the requirement to also limit 3D cultivation time. A possible restriction up until 28 days was considered to further reduce the non-responder rate. Indeed, between 29 and 42 days of cultivation, a non-responder rate of 50% indicates that further limitation of the cultivation time in 3D could improve the responder rate. In line with this, the non-responder rate was lower in the group when cultivation was restricted from 42 up until maximal 28 days; non-responder rate of 31.7% versus 26.6% respectively (cf. Table 2). Again, based on not only the non-responder rate but also the feasibility for spheroid cultivation time, the spheroid cultivation time was further restricted to a maximum of 28 days.

As expected from the separate assessments of ML and 3D cultivation times, the total cultivation time also correlated negatively with clinical outcome (FIG. 1C). In order to identify additive effects of ML and 3D during the manufacturing process, first the individual effects were excluded by eliminating batches that were cultivated over 16 days in P0 and over 28 days in 3D from the data set containing 52% non-responders (cf. Table 3). The group of spheroid batches that remained in the analysis, were cultivated equal or less than 55 days. In this group no correlation could be found between cultivation time and clinical outcome, thus demonstrating that no additive effects of P0 and 3D together were present when batches were cultivated within the newly defined cultivation times (FIG. 1F). Further restrictions based on non-responder rate would therefore only consider the influence of the entire cultivation time (ML+3D) on clinical efficacy or safety. The group of batches that have been cultivated up until 55 days showed a non-responder rate of 26.1% which is a significant improvement compared to the 31.7% of the total group of batches.

Therefore, the total cultivation time is to be limited to equal or less 55 than days in accordance with the best mode of the invention.

Altogether, these analyses demonstrate a high non-responder rate of batches with long cultivation times and underscore the need to adjust the operational ranges for chondrocyte cultivation times.

Considering the high occurrence of non-responders among patients that have been treated with batches with long cultivation times, the non-responder and responder groups were compared for extended cultivation times outside the newly defined limits. From this point on, only patients that were included in the study were further analysed, since this study group enables a comparison to the micro-fracture (MFX) treatment group. In the study, 25% (n=12) of the total patient group did not respond to the ACI treatment after 1 year after implantation. If we look at this group, two out of 12 (16.7%) non-responders appeared to have been cultivated longer than 16 days in P0, whereas for only 8.5% of the responder this was the case (n=3 out of 36). A more striking discrepancy was seen between non-responder and responder for prolonged 3D cultivation time; 7 out of 12 batches belonging to the group of non-responder (58.3%) have been cultivated in 3D longer than 28 days, whereas this was the case for only 16.6% of the responder batches (n=8). The over-representation of batches that were manufactured out of the newly restricted cultivation times in the non-responder groups (66.7%) compared to the responder groups (22.2%), demonstrates again the need to adjust the cultivation times. In the total group of the study 67% of the batches were produced according to the more stringent operational ranges (ORs), subgroup 1, and 33% of the batches have been produced outside the newly defined cultivation limits, subgroup 2.

If the operational ranges or process parameters would not be related to clinical efficacy, the distribution of batches that did not result in a clinical improvement after ACI, would have been equally distributed between the group of batches with short and long cultivation time. Therefore, these analyses indicate that the initial correlation analysis between KOOS and cultivation times and that the manufacturing process can cause, at least partly, loss of efficacy of the chondrocyte spheroids used for ACI.

If restriction of cell cultivation times is effective such that improvement of clinical efficacy of the ACI treatment can be expected, the possible improvement for study batches was quantified by comparison with the comparator MFX. After defining new limits for cell cultivation times in ML, 3D and total cultivation time, a retrospective assessment of the clinical data was conducted. Here, patients were divided into two groups. This division is based on the elimination of batches from the study data set as described before. The subgroups consist of spheroid batches that were either produced within the newly defined operational ranges for the process parameter P0, 3D and ML plus 3D, Subgroup 1, or out of these ranges, in at least one of the cultivation phases, Subgroup 2. The differences in cultivation times between the two subgroups are depicted in FIG. 2.

Figures 2A, 2B, 2C, 2D:
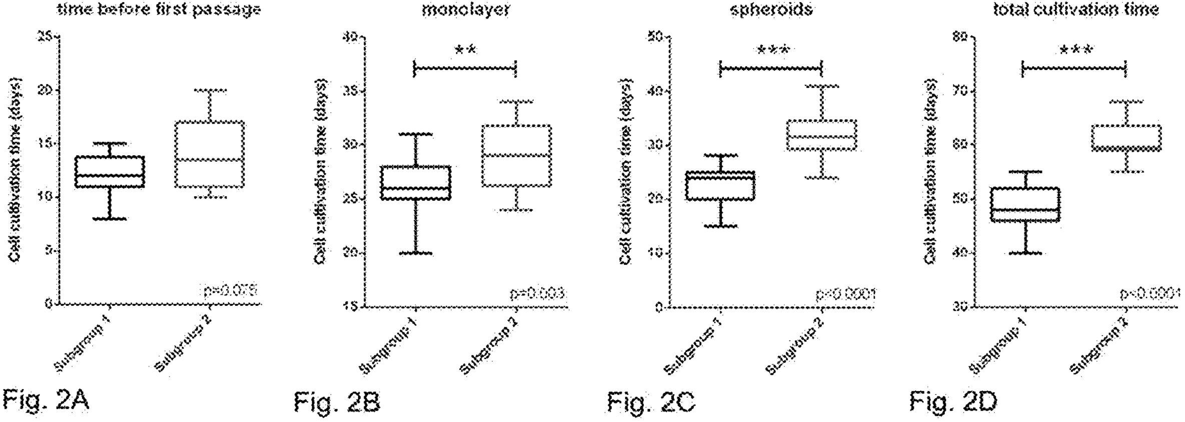
FIG. 2A illustrates the chondrocyte cultivation times before P0 in Subgroup 1 and Subgroup 2 of the study.
FIG. 2B illustrate the chondrocyte monolayer cultivation times in Subgroup 1 and Subgroup 2 of the study.
FIG. 2C illustrate the spheroid cultivation times in Subgroup 1 and Subgroup 2 of the study.
FIG. 2D illustrate the total cultivation times in Subgroup 1 and Subgroup 2 of the study.

Here, it is shown that the cultivation times in monolayer (ML) and 3D and the total cultivation time (ML plus 3D) were significantly longer in the batches of Subgroup 2 (FIG. 2B-D). For P0 however, there was no statistically significant difference between the two subgroups (FIG. 2A). This is due to the fact that some batches with extended 3D cultivation times, and therefore assigned to Subgroup 2, still had P0 cultivation time within the newly defined range.

Figures 3A, 3B, 3C, 3D:
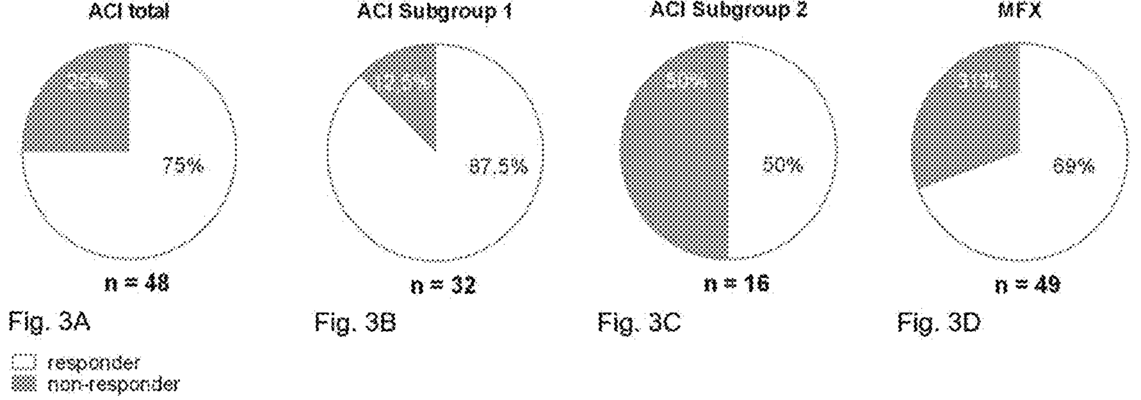
FIG. 3A illustrates the percentages of responders and non-responders in the total study population.
FIG. 3B illustrates the percentages of responders and non-responders in Subgroup 1 treated with spheroids produced with restricted cultivation times.
FIG. 3C illustrates the percentages of responders and non-responders in Subgroup 2 treated with spheroids produced with longer cultivation times.
FIG. 3D illustrates the percentages of responders and non-responders in patients treated with micro-fracture surgery (MFX)

Subgroup 1, consisting of 32 patients that were treated with chondrocyte spheroids produced with restricted cultivation times, was compared with the total group of study patients to find differences in clinical outcome. This subgroup contains a higher amount of responder of 87.5%, compared to 75% in the total study group (FIG. 3). In contrast, the subgroup of 16 patients that were treated with spheroid batches cultivated outside the newly defined operational ranges showed only 50% positive clinical outcome after 1 year after implantation (FIG. 3).

In order to compare the clinical improvement of patients treated with spheroids produced by the adjusted manufacturing process, a superiority analysis was performed between these batches and micro-fracture treatment (MFX), cf. Table 4.

TABLE 4

| | ACI | | ACI | |
|---|---|---|---|---|
| | Total | MFX | Subgroup 1 | Subgroup 2 |
| Number of patients | 48 | 49 | 32 | 16 |
| Mean KOOS overall delta | 22.16 | 16.09 | 26.63 | 13.22 |
| Std. Deviation | 18.29 | 15.16 | 18 | 15.98 |
| KOOS diff. of means vs MFX | 5.75 | — | 10.21 | −3.19 |
| Cl 95% diff of means | −1.03 | — | 2.53 | −12.56 |

Study clinical outcome after 1 year after implantation of the ACI product demonstrated to be non-inferior compared to micro-fracture (MFX) surgery (FIG. 4). The difference between the KOOS (overall delta) means of the chondrocyte spheroid-based ACI compared to MFX was in favour of the ACI treatment with 5.75 points after 1 year after implantation. With a confidence interval of 95% (CI 95%), a lower bound of −1.03 demonstrated non-inferiority of the ACI treatment compared to MFX (FIG. 4). In order to address a possible improvement of KOOS-based clinical outcome of the subgroup that has been manufactured within the newly defined operational ranges, the difference of the means between the ACI Subgroup 1 and MFX KOOS scores was calculated. This Subgroup of spheroid batches represents the current commercial manufacturing process of Spherox® and a mean difference of 10.21 compared to MFX (CI 95%) and a lower bound of 2.53 now showed superiority over MFX at (FIG. 4). Thus, the retrospective elimination of a specific group of batches with long cultivation times from the data set results in a higher average KOOS scores in this group.

The invention further relates to an implant, transplant and functional replacement tissue obtainable by the method according to the invention. The implant, transplant or functional replacement tissue produced in vitro or in vivo can be introduced into the surrounding native tissue of the recipient, preferably by injection. No cell division takes place in the spheroids produced by the method according to the invention, that is to say also in the implant, transplant or functional replacement tissue. If the functional tissue is introduced into native tissue, the spheroids then attach to the native tissue (adhesion) and migrate into the gaps (migration), but without dividing. An optimal supply/restoration is thus ensured, but without the risk of an uncontrolled proliferation of the functional replacement tissue. To this end, the obtained spheroids of the invention produced in vitro are injected into the diseased or degraded tissue. To do so, an injection needle or other suitable application system must have at least the diameter of the spheroids. Appropriate transport and injection systems are disclosed in applicant's DE102009025347A1 and EP2345450B1.

The invention also relates to a preparation, in particular a pharmaceutical preparation or a tissue preparation, a drug, a transplant or an implant consisting of or containing spheroids, which is obtainable by the method according to the invention and optionally further excipients and additives.

The invention also relates to pharmaceutical preparations, tissue preparations and drugs, in particular suspensions and solutions, in particular injection solutions, which contain the spheroids according to the invention and optionally further excipients and additives.

The invention also relates to the specific therapeutic/pharmaceutical use of a pharmaceutical preparation according to the invention, a tissue preparation, a drug according to the invention, a transplant according to the invention or implant according to the invention for treating cartilage defects and/or bone defects, in particular traumatic cartilage defects and/or bone defects, lesions, in particular traumatic lesions, cartilage degeneration, bone degeneration, osteoarthritis, and for therapeutic cartilage regeneration and/or bone regeneration in vivo.

The following figures and examples will explain the invention, but without limiting the invention to the figures and examples.

In total 120 patients of the study (supra) were used for statistical correlation analyses between clinical outcome and the operational ranges or process parameter. The primary endpoint to measure for clinical efficacy used in the study was the 'Knee injury and Osteoarthritis Outcome Scores' (KOOS) change from baseline. Data from 72 patients, 48 patients with ACI and 49 patients with MFX treatment were assessed in the present study and are provided in Table 5.

TABLE 5

Patient demographic data from the study

| | | ACI Subgroup 1 | ACI Subgroup 2 | ACI Total | MFX |
|---|---|---|---|---|---|
| number of patients | | 32 | 16 | 48 | 49 |
| Sex | male, n (%) | 21 (66%) | 9 (56%) | 30 (63%) | 27 (55%) |
| Age [years] | Mean (SD) | 35 (9) | 37 (10) | 36 (10) | 37 (9) |
| BMI [kg/m2] | Mean (SD) | 26.1 (3.2) | 25.0 (2.5) | 25.8 (3.1) | 25.9 (3.0) |
| | Min. | 19.0 | 21.0 | 19.0 | 18.2 |
| | Max. | 31.2 | 28.4 | 31.2 | 30.0 |
| Patient smoking habit | yes, n (%) | 9 (28%) | 3 (19%) | 12 (25%) | 19 (39%) |
| Defect size pre-debridement | Mean (SD) | 2.1 (0.7) | 2.4 (0.7) | 2.2 0.7) | 2.0 (0.8) |
| [cm2] day of arthroscopy | Min. | 0.5 | 1.0 | 0.5 | 0.8 |
| | Max. | 3.0 | 3.5 | 3.5 | 4.0 |
| Defect size post- | Mean (SD) | 2.7 (0.8) | 2.8 (0.7) | 2.7 (0.8) | n.a. |
| debridement [cm2] | Min. | 1.4 | 1.5 | 1.4 | n.a. |
| | Max. | 5.0 | 3.8 | 5 | n.a. |
| Defect location (primary) ICRS grade III or IV | Femur | 32 | 16 | 48 | 49 |
| Presence of further | Femur | 0 | 0 | 0 | 0 |
| defects < ICRS grade III | Tibia, n (%) | 2 (6%) | 1 (6%) | 3 (6%) | 3 (6%) |
| | Patella, n (%) | 6 (19%) | 4 (25%) | 10 (21%) | 10 (20%) |

ACI: autologous chondrocyte implantation.
MFX: micro-fracture surgery.
n: number.
BMI: body mass index.
SD: standard deviation.
Min.: minimum.
Max.: maximum.
N.a.: not annotated.
ICRS: International Cartilage Regeneration & Joint Preservation Society.

The overall KOOS score (including all subscales) before arthroscopy (=base line) and after 1 year after implantation were used [19]. The clinical outcome was defined as positive at a difference of at least 8 points between the two scores; overall change from baseline, and is based on the minimal important change (MIC) of 8-10 as described in the user's guide for KOOS questionnaires (www.koos.nu).

The operational ranges of monolayer cultivation times between the different cell culture passages, spheroid cultivation time and the total cultivation time used in the manufacturing process were statistically assessed against clinical outcome for every batch produced for the study.

To subsequently get insight if the newly defined ranges and limits used for cell culture times could have an effect on the product's efficacy, 48 patients of the study were divided into one group that were treated with batches produced according to the newly defined cell culture times (Subgroup 1) and a second group of batches that was produced outside these limits (Subgroup 2). Mean values of KOOS overall delta scores of respectively the total group, Subgroup 1 and Subgroup 2 were compared with the MFX group (Superiority analysis). Patient characteristics of the two subgroups are listed in Table 1.

Statistical Analysis

Differences between means were tested using Mann-Whitney's unpaired t-test (two-tailed, with P-value <0.05 considered significant). Correlation analyses were performed using Spearman's correlation coefficient, with a P<0.05 considered significant. Superiority/non-inferiority analysis of the ACI treatment compared to MFX treatment was performed by an unpaired t-test with Welch's correction with a 95% confidence interval. All statistical analyses were performed using GraphPad Prism v6 (GraphPad Software, USA).

FIG. 1. Clinical Outcome Correlate with Cell Cultivation Times

From 120 spheroid batches used in the study, the operational ranges were assessed against clinical outcome after 1 year after implantation. Long cultivation times in monolayer before the first passage (P0) (A), in 3D (spheroids) (B) and total in ML and 3D (C) correlated with low KOOS overall delta scores. Eliminating spheroid batches from the data set that were produced with long cultivation time resulted in loss of correlation in P0 (D), 3D (E) and total cultivation time (F). This enabled to set provisional limits (arrow) for maximum cultivation times such that cultivation time does not have a negative effect on the drug product's efficacy. Maximum cultivation time for P0 was set at 18 days (D), for 3D at 31 days (E) and for the total cultivation time in ML and 3d at 55 days (F). r=Spearman correlation efficient with a P-value <0.05 is considered significant. KOOS=Knee injury and Osteoarthritis Outcome Score.

FIG. 2. Chondrocyte Cultivation Times in Subgroup 1 and Subgroup 2 of the Study Study batches were divided into two subgroups; subgroup 1 that have been cultivated within the newly defined maximum cultivation times, and subgroup 2 that have been cultivated outside these limits. Spheroid batches were cultivated significantly longer in subgroup 2 considering ML total cultivation time, P=0.003 (B), 3D, P<0.001 (C) and total cultivation time in ML and 3D, P<0.001 (D). In P0 (A), cultivation time was not significantly different between the two subgroups (P=0.075) because this subgroup contains batches with long 3D cultivation time (>28 days) that have been cultivated within the ORs in P0 (<16 days). Means between groups were analysed using the Mann-Witney t-test (two-sided) with P-value <0.05 considered significant.

FIG. 3. Spheroid Batches with Short Cultivation Times Show Improved Responder Rate The patients that underwent ACI were divided into two subgroups: Subgroup 1 consisting of patients treated with spheroid batches manufactured with restricted cultivation times, and Subgroup 2 that were treated with spheroid batches with longer cultivation times. A: From the total study group of patients, 75% of the spheroid batches belong to responder patients (KOOS>8). B: In subgroup 1, 87.5% of the patients showed a relevant clinical improvement (KOOS>8), whereas in subgroup 2 (C) only 50% of the patients. D: In the study comparator group (MFX) 69% of the patients showed a clinical improvement after 1 year (KOOS>8).

FIG. 4. Superiority/Non-Inferiority Analysis of Subgroup 1 and 2

The clinical outcome from patients included in the study, 1 year after transplantation shows non-inferiority compared to microfracture (MFX). The two subgroups derived from the study that contains spheroid batches either cultivated within the newly defined ORs, Subgroup 1, or outside the newly defined ORs, Subgroup 2. The means of KOOS overall delta scores of the total group of patients, Subgroup 1 and Subgroup 2 were compared with the mean KOOS overall delta scores of the MFX treated patients, 1 year after treatment. The retrospective selection of spheroid batches that have been manufactured within the more restricted cultivation times results in the selection of patients with a clinical outcome that show superiority over MFX treatment.

FIG. 5A, 5B Longer Chondrocyte Cultivation Times in the Group of Non-Responder Patients From 120 patients that were included in the study, the non-responder patients (KOOS overall delta score <8) received spheroid batches that were produced with significantly longer cultivation times in P0 (A) and total cultivation times (B). Mann-Witney t-test with $p<0.05$ considered significant. P0=monolayer cultivation time of isolated chondrocytes before the first passage.

Table 1: Defining the operational ranges (OR) of the inventive process using the non-responder rate in relation to cell cultivation time. Patient IDs in grey, marked with 'N' correspond to non-responder patients (KOOS<8).

Table 2: Defining the operational ranges (OR) of the inventive process using the non-responder rate in relation to spheroid cultivation time. Patient IDs in grey, marked with 'N' correspond to non-responder patients (KOOS<8).

Table 3: Defining the operational ranges (OR) of the inventive process using the non-responder rate in relation to total cultivation time (monolayer and 3D). Patient IDs in grey, marked with IN' correspond to non-responder patients (KOOS<8).

FURTHER REFERENCES

Niemeyer P, Laute V, John T, Becher C, Diehl P, Kolombe T, et al. The Effect of Cell Dose on the Early Magnetic Resonance Morphological Outcomes of Autologous Cell Implantation for Articular Cartilage Defects in the Knee: A Randomized Clinical Trial. Am J Sports Med 2016.

Becher C, Laute V, Fickert S, Zinser W, Niemeyer P, John T, et al. Safety of three different product doses in autologous chondrocyte implantation: results of a prospective, randomised, controlled trial. J Orthop Surg Res 2017; 12: 71.

Schubert T, Anders S, Neumann E, Scholmerich J, Hofstadter F, Grifka J, et al. Long-term effects of chondrospheres on cartilage lesions in an autologous chondrocyte implantation model as investigated in the SCID mouse model. Int J Mol Med 2009; 23: 455-460

TABLE 1

| Patient ID | R/N | PO (days) | non-responder (%) | |
|---|---|---|---|---|
| All patients: | | 7-28 | 31.7% | |
| Patients new OR: | | ≤16 | 28% | |
| 2253 | N | 28 | | |
| 2205 | R | 20 | | |
| 2207 | N | 20 | 80% | |
| 2427 | N | 20 | | |
| 2204 | N | 19 | | |
| 1101 | N | 18 | | |
| 2277 | R | 18 | | 61.5% |
| 1113 | N | 17 | | |
| 1305 | N | 17 | 50% | |
| 1804 | R | 17 | | |
| 2220 | N | 17 | | |
| 2434 | R | 17 | | |
| 2440 | R | 17 | | |
| 2103 | R | 16 | | |
| 1322 | R | 15 | | |
| 2104 | R | 15 | | |
| 2417 | N | 15 | | |
| 1104 | N | 14 | | |
| 1321 | N | 14 | | |
| 2102 | N | 14 | | |
| 2216 | R | 14 | | |
| 2217 | N | 14 | | |
| 2219 | R | 14 | | |
| 2223 | R | 14 | | |
| 2286 | R | 14 | | |
| 2294 | R | 14 | | |
| 2301 | R | 14 | | |
| 2418 | R | 14 | | |
| 2420 | R | 14 | | |
| 2423 | N | 14 | | |
| 2431 | N | 14 | | |
| 1102 | R | 13 | | |
| 1114 | R | 13 | | |
| 1201 | R | 13 | | |
| 1205 | N | 13 | | |
| 1802 | R | 13 | | |
| 1808 | R | 13 | | |
| 2231 | R | 13 | | |
| 2235 | N | 13 | | |
| 2246 | N | 13 | | |
| 2265 | N | 13 | | |
| 2283 | N | 13 | | |
| 2412 | N | 13 | | |
| 2435 | R | 13 | | |
| 2441 | R | 13 | | |
| 2601 | R | 13 | | |
| 2709 | R | 13 | | |
| 1118 | R | 12 | | |
| 1120 | R | 12 | | |
| 1311 | N | 12 | | |
| 1603 | R | 12 | | |
| 1607 | N | 12 | | |
| 1609 | N | 12 | | |
| 1702 | N | 12 | | |
| 1707 | R | 12 | | |
| 2251 | R | 12 | | |
| 2275 | N | 12 | | |
| 2409 | R | 12 | | |
| 2410 | R | 12 | | |
| 2411 | N | 12 | | |
| 2439 | R | 12 | | |
| 2805 | N | 12 | | |
| 1105 | R | 11 | | |
| 1107 | R | 11 | | |
| 1108 | R | 11 | | |
| 1116 | N | 11 | | |
| 1122 | R | 11 | | |
| 1126 | R | 11 | | |
| 1207 | N | 11 | | |
| 1304 | R | 11 | | |
| 1306 | N | 11 | | |
| 1309 | R | 11 | | |
| 1310 | N | 11 | | |
| 2201 | R | 11 | | |
| 2203 | R | 11 | | |
| 2209 | R | 11 | | |

TABLE 1-continued

| Patient ID | R/N | PO (days) | non-responder (%) |
|---|---|---|---|
| 2221 | R | 11 | |
| 2222 | R | 11 | |
| 2224 | R | 11 | |
| 2226 | R | 11 | |
| 2244 | N | 11 | |
| 2254 | R | 11 | |
| 2255 | R | 11 | |
| 2257 | R | 11 | |
| 2263 | R | 11 | |
| 2269 | N | 11 | |
| 2402 | R | 11 | |
| 2408 | R | 11 | |
| 2424 | R | 11 | |
| 2701 | N | 11 | |
| 1106 | R | 10 | |
| 1109 | R | 10 | |
| 1117 | R | 10 | |
| 1301 | R | 10 | |
| 1312 | R | 10 | |
| 1602 | R | 10 | |
| 1803 | R | 10 | |
| 2202 | R | 10 | |
| 2229 | R | 10 | |
| 2238 | R | 10 | |
| 2239 | R | 10 | |
| 2240 | R | 10 | |
| 2241 | R | 10 | |
| 2248 | R | 10 | |
| 2249 | R | 10 | |
| 2252 | R | 10 | |
| 2260 | N | 10 | |
| 2261 | R | 10 | |
| 2273 | R | 10 | |
| 2284 | R | 10 | |
| 2287 | R | 10 | |
| 2413 | N | 10 | |
| 1112 | R | 9 | |
| 1123 | R | 9 | |
| 1204 | R | 9 | |
| 2407 | N | 9 | |
| 1307 | R | 8 | |
| 2706 | R | 8 | |
| 2256 | R | 7 | |
| 2259 | R | 7 | |

R: responder.

N: non-responder.

OR: operational ranges.

TABLE 2

| Patient ID | R/N | 3D cultivation time (days) | non-responder (%) | |
|---|---|---|---|---|
| All patients: | | 15-42 | 31.7% | |
| Patients new OR: | | ≤28 | 26.6% | |
| 1201 | R | 42 | | |
| 2269 | N | 41 | | |
| 1207 | N | 39 | | |
| 1312 | R | 39 | | |
| 1804 | R | 38 | | |
| 2235 | N | 38 | | |
| 2248 | R | 35 | | |
| 2287 | R | 35 | 59% | |
| 2402 | R | 35 | | |
| 2221 | R | 34 | | |
| 2407 | N | 34 | | 50% |
| 2417 | N | 33 | | |
| 2423 | N | 33 | | |
| 2246 | N | 32 | | |
| 2253 | N | 32 | | |
| 2265 | N | 32 | | |
| 2283 | N | 32 | | |
| 1107 | R | 31 | | |
| 2104 | R | 31 | | |
| 2217 | N | 31 | | |
| 2256 | R | 31 | 33% | |
| 2263 | R | 31 | | |
| 2434 | R | 31 | | |
| 1101 | N | 30 | | |
| 2701 | N | 30 | | |
| 2418 | R | 29 | | |
| 1120 | R | 28 | | |
| 1310 | N | 28 | | |
| 2220 | N | 28 | | |
| 2229 | R | 28 | | |
| 2238 | R | 28 | | |
| 2239 | R | 28 | | |
| 2249 | R | 28 | | |
| 2273 | R | 28 | | |
| 2439 | R | 28 | | |
| 1102 | R | 27 | | |
| 1306 | N | 27 | | |
| 2224 | R | 27 | | |
| 2241 | R | 27 | | |
| 2251 | R | 27 | | |
| 2254 | R | 27 | | |
| 2257 | R | 27 | | |
| 2277 | R | 27 | | |
| 2441 | R | 27 | | |
| 2805 | N | 27 | | |
| 1113 | N | 26 | | |
| 1609 | N | 26 | | |
| 2240 | R | 26 | | |
| 2252 | R | 26 | | |
| 2408 | R | 26 | | |
| 1123 | R | 25 | | |
| 1205 | N | 25 | | |
| 2205 | R | 25 | | |
| 2207 | N | 25 | | |
| 2244 | N | 25 | | |
| 2260 | N | 25 | | |
| 2261 | R | 25 | | |
| 2420 | R | 25 | | |
| 2435 | R | 25 | | |
| 2440 | R | 25 | | |
| 1126 | R | 24 | | |
| 1307 | R | 24 | | |
| 1322 | R | 24 | | |
| 1808 | R | 24 | | |
| 2103 | R | 24 | | |
| 2223 | R | 24 | | |
| 2231 | R | 24 | | |
| 2259 | R | 24 | | |
| 2286 | R | 24 | | |
| 2294 | R | 24 | | |
| 2427 | N | 24 | | |
| 2706 | R | 24 | | |
| 1105 | R | 23 | | |
| 1108 | R | 23 | | |
| 1116 | N | 23 | | |
| 1122 | R | 23 | | |

TABLE 2-continued

| Patient ID | R/N | 3D cultivation time (days) | non-responder (%) |
|---|---|---|---|
| 1204 | R | 23 | |
| 1309 | R | 23 | |
| 2410 | R | 23 | |
| 2424 | R | 23 | |
| 1109 | R | 22 | |
| 1112 | R | 22 | |
| 1304 | R | 22 | |
| 1305 | N | 22 | |
| 1603 | R | 22 | |
| 1607 | N | 22 | |
| 2301 | R | 22 | |
| 1114 | R | 21 | |
| 1707 | R | 21 | |
| 1802 | R | 21 | |
| 2202 | R | 21 | |
| 2204 | N | 21 | |
| 2255 | R | 21 | |
| 2275 | N | 21 | |
| 2409 | R | 21 | |
| 1106 | R | 20 | |
| 1117 | R | 20 | |
| 1311 | N | 20 | |
| 1702 | N | 20 | |
| 1803 | R | 20 | |
| 2201 | R | 20 | |
| 2203 | R | 20 | |
| 2209 | R | 20 | |
| 2222 | R | 20 | |
| 2226 | R | 20 | |
| 2284 | R | 20 | |
| 2413 | N | 20 | |
| 2431 | N | 20 | |
| 2601 | R | 20 | |
| 2709 | R | 20 | |
| 1118 | R | 19 | |
| 2102 | N | 19 | |
| 2411 | N | 19 | |
| 2412 | N | 19 | |
| 1104 | N | 18 | |
| 1321 | N | 18 | |
| 2216 | R | 17 | |
| 2219 | R | 17 | |
| 1301 | R | 16 | |
| 1602 | R | 15 | |

R: responder.

N: non-responder.

OR: operational ranges.

TABLE 3

| Patient ID | R/N | ML + 3D cultivation time (days) | non-responder (%) |
|---|---|---|---|
| All patients: | | 39-76 | 31.7% |
| Patients new OR: | | ≤55 | 26% |

TABLE 3-continued

| Patient ID | R/N | ML + 3D cultivation time (days) | non-responder (%) |
|---|---|---|---|
| 1804 | R | 76 | 50% (1804–1120) |
| 2253 | N | 74 | |
| 1201 | R | 73 | |
| 1312 | R | 68 | |
| 1207 | N | 67 | |
| 2235 | N | 66 | |
| 2269 | N | 66 | |
| 2434 | R | 65 | |
| 2417 | N | 64 | |
| 1101 | N | 62 | |
| 2423 | N | 62 | |
| 2104 | R | 61 | |
| 2402 | R | 61 | |
| 2418 | R | 60 | |
| 2217 | N | 59 | |
| 2220 | N | 59 | |
| 2221 | R | 59 | |
| 2246 | N | 59 | |
| 2248 | R | 59 | |
| 2263 | R | 59 | |
| 2265 | N | 59 | |
| 2277 | R | 59 | |
| 2283 | N | 59 | |
| 2287 | R | 59 | |
| 2427 | N | 58 | |
| 1107 | R | 56 | |
| 2407 | N | 56 | |
| 2440 | R | 56 | |
| 1120 | R | 55 | |
| 1322 | R | 55 | |
| 2701 | N | 55 | |
| 1102 | R | 54 | |
| 1310 | N | 54 | |
| 2408 | R | 54 | |
| 2420 | R | 54 | |
| 2441 | R | 54 | |
| 2805 | N | 54 | |
| 1104 | N | 53 | |
| 1113 | N | 53 | |
| 1306 | N | 53 | |
| 1808 | R | 53 | |
| 2103 | R | 53 | |
| 2251 | R | 53 | |
| 2439 | R | 53 | |
| 1205 | N | 52 | |
| 2204 | N | 52 | |
| 2205 | R | 52 | |
| 2207 | N | 52 | |
| 2223 | R | 52 | |
| 2224 | R | 52 | |
| 2229 | R | 52 | |
| 2231 | R | 52 | |
| 2238 | R | 52 | |
| 2239 | R | 52 | |
| 2240 | R | 52 | |
| 2241 | R | 52 | |
| 2244 | N | 52 | |
| 2249 | R | 52 | |
| 2252 | R | 52 | |
| 2254 | R | 52 | |
| 2256 | R | 52 | |
| 2257 | R | 52 | |
| 2273 | R | 52 | |
| 2286 | R | 52 | |
| 2294 | R | 52 | |
| 2435 | R | 52 | |
| 1126 | R | 49 | |
| 1603 | R | 49 | |
| 1609 | N | 49 | |
| 1105 | R | 48 | |
| 1108 | R | 48 | |
| 1114 | R | 48 | |
| 1116 | N | 48 | |
| 1122 | R | 48 | |
| 1309 | R | 48 | |
| 1607 | N | 48 | |

TABLE 3-continued

| Patient ID | R/N | ML + 3D cultivation time (days) | non-responder (%) |
|---|---|---|---|
| 1802 | R | 48 | |
| 1803 | R | 48 | |
| 2410 | R | 48 | |
| 2424 | R | 48 | |
| 1112 | R | 47 | |
| 1117 | R | 47 | |
| 1118 | R | 47 | |
| 1304 | R | 47 | |
| 1311 | N | 47 | |
| 1321 | N | 47 | |
| 1707 | R | 47 | |
| 2102 | N | 47 | |
| 2409 | R | 47 | |
| 2411 | N | 47 | |
| 2431 | N | 47 | |
| 2706 | R | 47 | |
| 2709 | R | 47 | |
| 1204 | R | 46 | |
| 1305 | N | 46 | |
| 1307 | R | 46 | |
| 1702 | N | 46 | |
| 2412 | N | 46 | |
| 2601 | R | 46 | |
| 1109 | R | 45 | |
| 1123 | R | 45 | |
| 2201 | R | 45 | |
| 2202 | R | 45 | |
| 2203 | R | 45 | |
| 2209 | R | 45 | |
| 2216 | R | 45 | |
| 2219 | R | 45 | |
| 2222 | R | 45 | |
| 2226 | R | 45 | |
| 2255 | R | 45 | |
| 2259 | R | 45 | |
| 2260 | N | 45 | |
| 2261 | R | 45 | |
| 2275 | N | 45 | |
| 2284 | R | 44 | |
| 2413 | N | 44 | |
| 1106 | R | 43 | |
| 1301 | R | 40 | |
| 1602 | R | 40 | |
| 2301 | R | 39 | |

R: responder.
N: non-responder.
OR: operational ranges.

The invention claimed is:

1. A method for propagating or enriching cartilage cells and providing spheroids thereof comprising the steps:

(a) obtaining cartilage cells from tissue of human or animal origin as starting material, (b) cultivating the cartilage cells from step (a) as a monolayer (2D) on a substrate up to a first passage, (b1) passaging and cultivating the cartilage cells from step (b) as a monolayer (2D) on a substrate, (c) taking the cultivated cartilage cells from the monolayer from step (b1) and cultivating said cultivated cartilage cells in a suspension in a 3D environment to form spheroids, and (d) collecting the spheroids, wherein the total cultivation time of step (b), step (b1), and step (c) is equal to or less than 55 days, the time duration of step (b) is more than 10 days and equal to or less than 16 days, and the time duration of step (c) is from 15 days to less than 28 days.

2. The method according to claim 1, wherein the spheroids consist of more than 3,000 cells.

3. The method according to claim 1, wherein the spheroids consist of cells in the range of 3,000 to 200,000 cells.

4. The method according to claim 1, wherein the spheroids consist of cells in the range of 3,500 to 75,000 cells.

5. The method according to claim 1, wherein the spheroids have a diameter in the range of 100 to 1,000 μm.

6. The method according to claim 1, wherein the spheroids have a diameter in the range of 200 to 900 μm.

7. The method according to claim 1, wherein the spheroids have a diameter in the range of 240 to 870 μm.

8. The method according to claim 1, wherein the spheroids, during use for the treatment of patients having cartilage defects or bone defects, display a reduced number of non-responders or therapeutic failures among the treated patients, as compared to spheroids produced by a method in which the total cultivation time of step (b), step (b1), and step (c) is greater than 55 days, the time duration of step (b) is 10 days or less or greater than 16 days, or the time duration of step (c) is less than 15 days or greater than or equal to 28 days.

9. The method according to claim 8, wherein the cartilage defects or bone defects are traumatic cartilage defects or traumatic bone defects or lesions.

10. The method according to claim 8, wherein the non-responders or therapeutic failures among the treated patients have a Knee injury and Osteoarthritis Outcome Score (KOOS) below 8.

11. The method according to claim 1, wherein the spheroids, during use for the treatment of patients having traumatic cartilage or bone lesions, cartilage degeneration, bone degeneration, osteoarthritis, or for therapeutic cartilage regeneration or bone regeneration in vivo, display a reduced number of non-responders or therapeutic failures among the treated patients, as compared to spheroids produced by a method in which the total cultivation time of step (b), step (b1), and step (c) is greater than 55 days, the time duration of step (b) is 10 days or less or greater than 16 days, or the time duration of step (c) is less than 15 days or greater than or equal to 28 days.

* * * * *